(12) United States Patent
Ito et al.

(10) Patent No.: US 9,157,896 B2
(45) Date of Patent: Oct. 13, 2015

(54) ULTRASONIC FLAW DETECTING APPARATUS AND ULTRASONIC FLAW DETECTING METHOD

(75) Inventors: Yoshino Ito, Kawasaki (JP); Hirokazu Karasawa, Yokohama (JP); Yoshio Ueda, Suita (JP); Tsuyoshi Hieda, Nishinomiya (JP); Tetsuya Yadoguchi, Kitakyushu (JP); Tetsuo Kawakami, Kitakyushu (JP); Kouichi Kokubo, Kitakyushu (JP); Hideo Isobe, Suginami-Ku (JP); Kazuyuki Haruna, Sakai (JP); Masamitsu Niki, Kobe (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 1168 days.

(21) Appl. No.: 13/070,155

(22) Filed: Mar. 23, 2011

(65) Prior Publication Data
US 2011/0232386 A1      Sep. 29, 2011

(30) Foreign Application Priority Data

Mar. 25, 2010   (JP) ................................. 2010-069348

(51) Int. Cl.
| | | |
|---|---|---|
| *G01N 29/06* | (2006.01) | |
| *G01N 29/38* | (2006.01) | |
| *G01N 29/40* | (2006.01) | |

(52) U.S. Cl.
CPC .............. *G01N 29/069* (2013.01); *G01N 29/38* (2013.01); *G01N 29/40* (2013.01); *G01N 2291/106* (2013.01)

(58) Field of Classification Search
CPC . G01N 29/043; G01N 29/06; G01N 29/0654; G01N 29/069; G01N 29/38; G01N 29/36; G01N 29/40

USPC .......... 73/609, 610, 611, 612, 614, 615, 616, 73/602
See application file for complete search history.

(56) References Cited

U.S. PATENT DOCUMENTS

| | | | | |
|---|---|---|---|---|
| 3,986,389 A | * | 10/1976 | Mesina et al. | .................. 73/611 |
| 4,432,235 A | * | 2/1984 | Renzel et al. | .................. 73/611 |

(Continued)

FOREIGN PATENT DOCUMENTS

| | | |
|---|---|---|
| CA | 2 277 460 A1 | 1/2001 |
| DE | 34 18 486 C1 | 1/1986 |

(Continued)

OTHER PUBLICATIONS

Ryoichi Arai, et al., "Large-Scale 3D Ultrasonic Inspection System", Toshiba Review, vol. 62, No. 8, Aug. 1, 2007, pp. 57-61 (With English Abstract).

(Continued)

*Primary Examiner* — Laura Martin
*Assistant Examiner* — Rose M Miller
(74) *Attorney, Agent, or Firm* — Oblon, McClelland, Maier & Neustadt, L.L.P.

(57) ABSTRACT

An ultrasonic flaw detecting apparatus including: a transducer including a piezoelectric element array for transmitting ultrasonic waves to and receiving echo signals from a test object; an element driving unit for scanning the piezoelectric element array at a predetermined cycle and generating the ultrasonic waves; a synthesizing unit for synthesizing an internal image of the test object based on the echo signals received by the piezoelectric element array; and a signal replacing unit for replacing the received echo signal with an echo signal in which a bottom echo of the test object is removed.

10 Claims, 11 Drawing Sheets

(56) References Cited

U.S. PATENT DOCUMENTS

| | | | |
|---|---|---|---|
| 6,474,163 B1 * | 11/2002 | Takada et al. | 73/600 |
| 6,981,417 B1 * | 1/2006 | Oravecz | 73/619 |
| 7,562,576 B2 * | 7/2009 | Fetzer et al. | 73/614 |
| 2006/0219013 A1 | 10/2006 | Baba et al. | |
| 2007/0084288 A1 * | 4/2007 | Thomas | 73/627 |
| 2010/0106432 A1 * | 4/2010 | Kitazawa et al. | 702/39 |

FOREIGN PATENT DOCUMENTS

| | | |
|---|---|---|
| DE | 10 2009 022 770 A1 | 11/2010 |
| JP | 2-213330 | 8/1990 |
| JP | 3-248058 | 11/1991 |
| JP | 2001-269341 | 10/2001 |
| JP | 2003-299066 | 10/2003 |
| JP | 2005-106782 | 4/2005 |
| JP | 2005106782 A * | 4/2005 |
| JP | 2005-156305 | 6/2005 |
| JP | 2005156305 A * | 6/2005 |
| JP | 2006-162321 | 6/2006 |

OTHER PUBLICATIONS

German Office Action issued May 13, 2013 in Patent Application No. 10 2011 014 957.0 with English Translation.

Alan J. Hunter et al., "Autofocusing Ultrasonic Imagery for Non-destructive Testing and Evaluation of Specimens with Complicated Geometries", NDT & E International, vol. 43, 2010, pp. 78-85.

Mitsuaki Katoh et al., "Materials Evaluation of Diffusion Bonded Steel Bar and its Impact Characteristics", NDT & E International, vol. 35, 2002, pp. 263-271.

Office Action issued Apr. 14, 2015 in Canadian Patent Application No. 2,734,635.

* cited by examiner

FIG. 5(A)
BEFORE PROCESSED

FIG. 5(B)
PROCESSING ONLY IN INTENSITY DIRECTION

FIG. 5(C)
AFTER PROCESSED

FIG. 6(A)

FIG. 6(B)
WITH SIGNAL PROCESSING

FIG. 6(C)
WITHOUT SIGNAL PROCESSING

ULTRASONIC FLAW DETECTING APPARATUS AND ULTRASONIC FLAW DETECTING METHOD

CROSS-REFERENCE TO RELATED APPLICATIONS

This application is based upon and claims the benefit of priority from Japanese Patient application No. 2010-069348, filed on Mar. 25, 2010, the entire contents of each of which are incorporated herein by reference.

FIELD

The present invention relates to an ultrasonic flaw detecting technique that visualizes a flaw state in a structure or a component such as a void and crack of a joint region by using an ultrasonic wave transmitted/received by a piezoelectric element.

BACKGROUND

It is widely practiced to use an ultrasonic flaw detecting apparatus to evaluate a flaw state such as a void and a crack of a joint region in a structure or a component that is a test object. An ultrasonic wave transmitted from a piezoelectric element to such a test object is reflected chiefly by a surface, a flaw, and a bottom of the object and the piezoelectric element receives echo signals from them. Assuming that a moment a surface echo has been received is a starting point and a moment a bottom echo is received is an ending point, an echo signal that is received within a range from the starting point to the ending point is treated as a flaw echo. Then, information such as a position and a size of the flaw in the test object is visualized by detecting intensity and a timing of the flaw echo (for example, see Patent Document 1 (Japanese Patent Laid-Open No. 2003-121426)).

It is known that in an ultrasonic flaw detecting apparatus, spatial resolution of a detected flaw decreases with increasing depth of a test object. Therefore, conventional ultrasonic flaw detecting apparatuses have a problem that if a flaw is at or near a bottom or a corner of a test object, visibility of a visualized flaw decreases because multiple echoes interfere with a flaw echo (see FIG. 6(C)).

The present invention has been made in view of such circumstances, and provided an ultrasonic flaw detecting technique that can accurately and rapidly detect a flaw at or near a bottom or a corner of a test object.

DETAILED DESCRIPTION

First Embodiment

Hereinafter, some embodiments will be described with reference to the accompanying drawings.

An ultrasonic flaw detecting apparatus comprising: a transducer 2 in which a piezoelectric element array 25 for transmitting ultrasonic waves to and receiving echo signals from a test object 3; an element driving unit 11 for scanning the piezoelectric element array 25 at a predetermined cycle and causing the ultrasonic waves; a synthesizing unit 15 for synthesizing an internal image of the test object 3 based on the echo signals received by the piezoelectric element array 25; and a signal replacing unit 17 for replacing the received echo signal with an echo signal in which a bottom echo of the test object 3 is removed.

Figure 1:
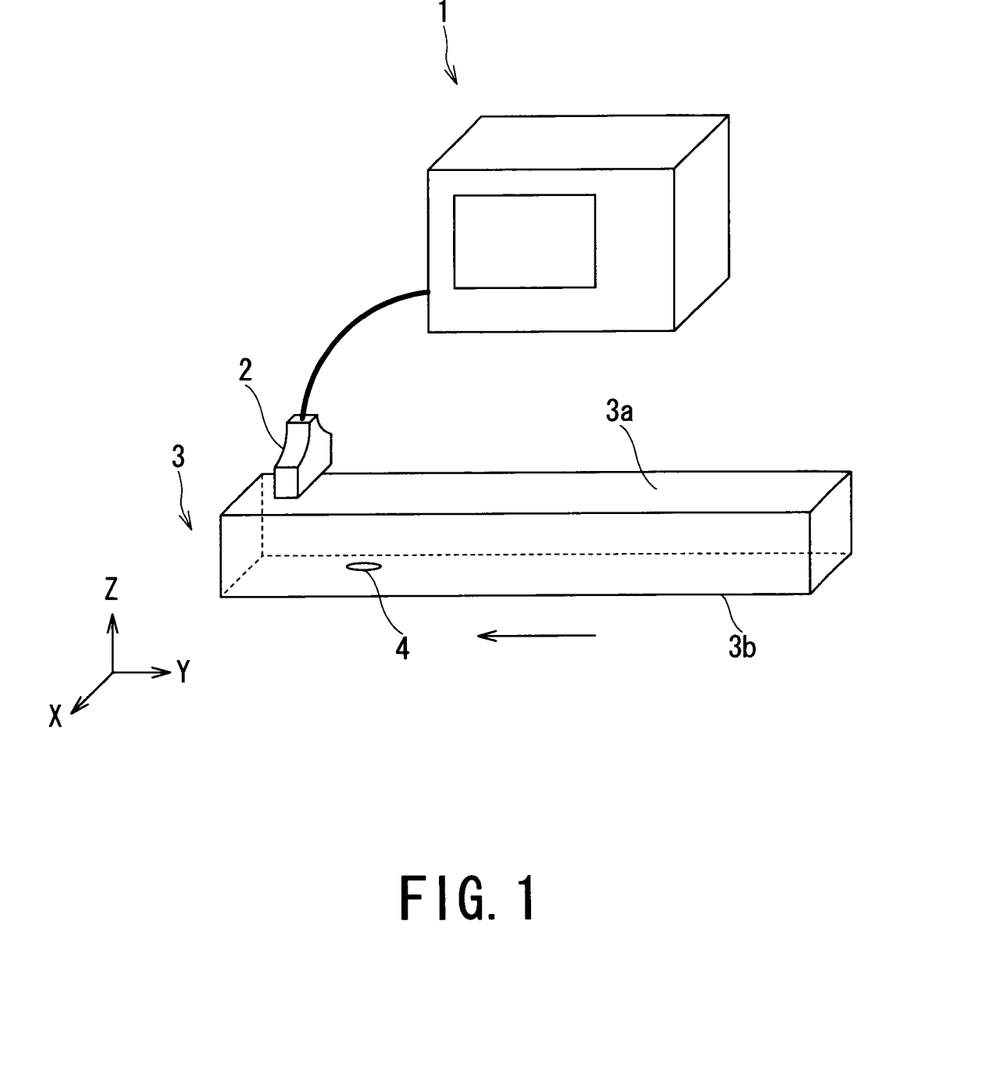
FIG. 1 illustrates an embodiment of an ultrasonic flaw detecting method for inspecting a test object (a square billet) by an ultrasonic flaw detecting apparatus.

As illustrated in FIG. 1, the ultrasonic flaw detecting apparatus in accordance with the present embodiment includes a main body 1 connected with a transducer 2 via a cable.

The ultrasonic flaw detecting apparatus abuts the transducer 2 on a surface 3a of a bar of steel (a square billet 3) that is a test object 3, and moves the square billet 3 to synthesize an internal three-dimensional image by a synthetic aperture focusing technique.

Consequently, the ultrasonic flaw detecting method for online detecting of a flaw 4 in the square billet 3 is achieved.

Figure 2:
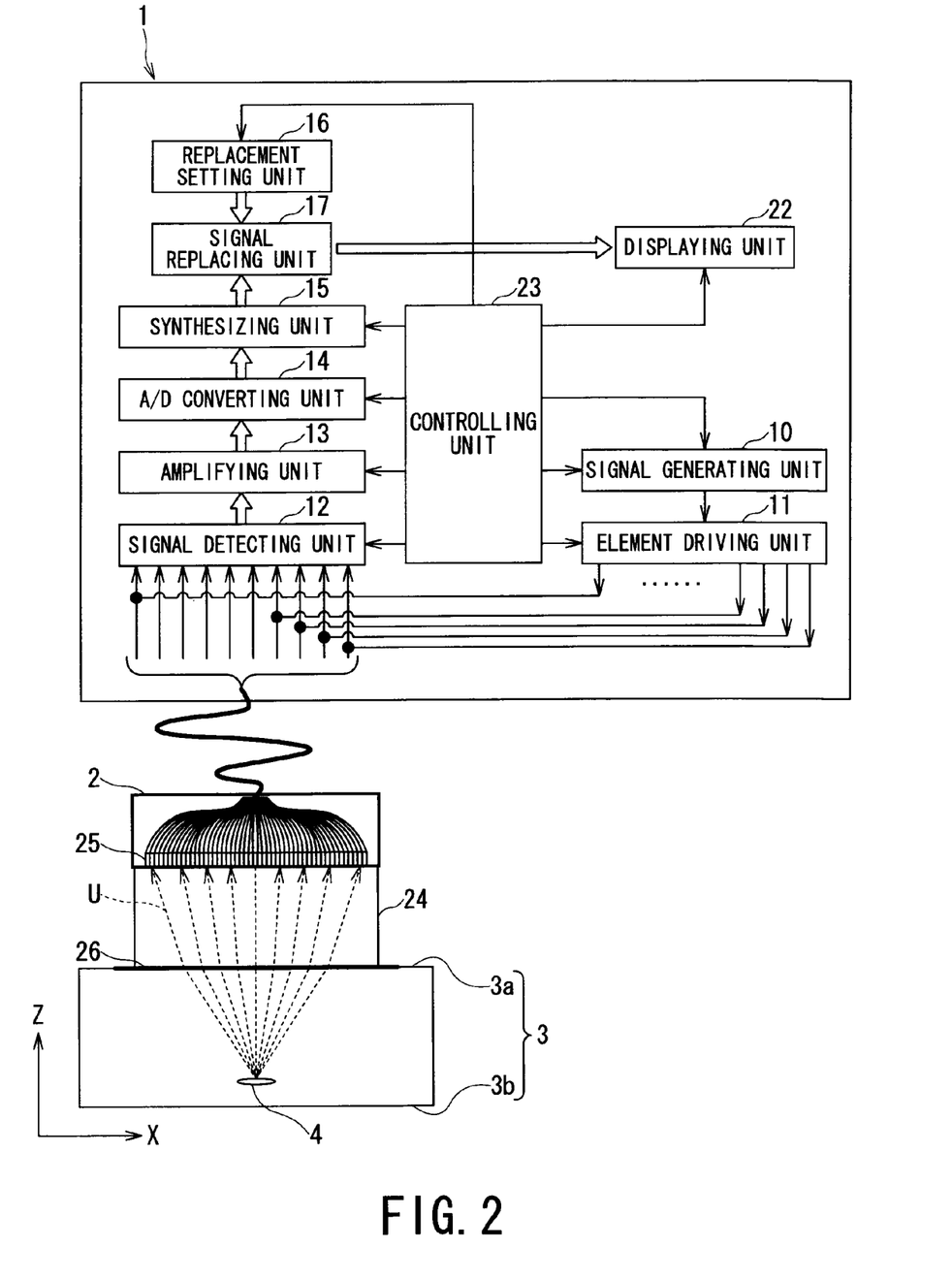
FIG. 2 is a block diagram of an ultrasonic flaw detecting apparatus in accordance with a first embodiment.

As shown in FIG. 2, in the transducer 2, a piezoelectric element array 25 for transmitting ultrasonic waves and receiving echo signals to and from the square billet 3. These piezoelectric elements of the array 25 are disposed in a linear arrangement in a direction (X axis direction), which is perpendicular to a moving direction of the square billet 3 (Y axis direction). Note that the piezoelectric elements array 25 may be disposed in a row or a matrix arrangement.

An ultrasonic wave is transmitted into the square billet 3 through a shoe 24 in contact with a front of the transducer 2 and a couplant 26, which is a sound propagation medium composed of liquid. Then, the transmitted ultrasonic wave turns into echo signals U including a flaw echo reflected from the flaw 4 in the square billet 3, a surface echo reflected from a surface 3a and a bottom echo reflected from a bottom 3b, and these echoes signals U are received at the transducer 2.

As shown in FIG. 2, the main body 1 of the ultrasonic flaw detecting apparatus includes a signal generating unit 10, an element driving unit 11, a signal detecting unit 12, an amplifying unit 13, an A/D converting unit 14, a synthesizing unit 15, a replacement setting unit 16, a signal replacing unit 17, a displaying unit 22, and a controlling unit 23 for controlling operations of these function units.

Such a configuration of the main body 1 allows for imaging the flaw 4 based on the synthetic aperture focusing technique (SAFT).

The SAFT is a technique that identifies a location of the flaw 4 by focusing on the fact that the flaw 4 exists on an arc having a radius of a propagation distance from, as a center, a piezoelectric element array 25 that receives a flaw echo and sequentially shifting a position of a piezoelectric element array 25 that transmits an ultrasonic wave.

The signal generating unit 10 generates sequential pulsed electrical signals so that the piezoelectric elements array 25 causing ultrasonic waves. The generated electrical signals are sent to the element driving unit 11 and sequentially input to a selected piezoelectric element of the array 25, and the ultrasonic scans are performed.

The piezoelectric element of the array 25, by nature of a piezoelectric body, generates an ultrasonic wave if the element receives an electrical signal, and conversely, if an ultrasonic wave is received, the piezoelectric element array 25 outputs an electrical signal.

Figure 3A:
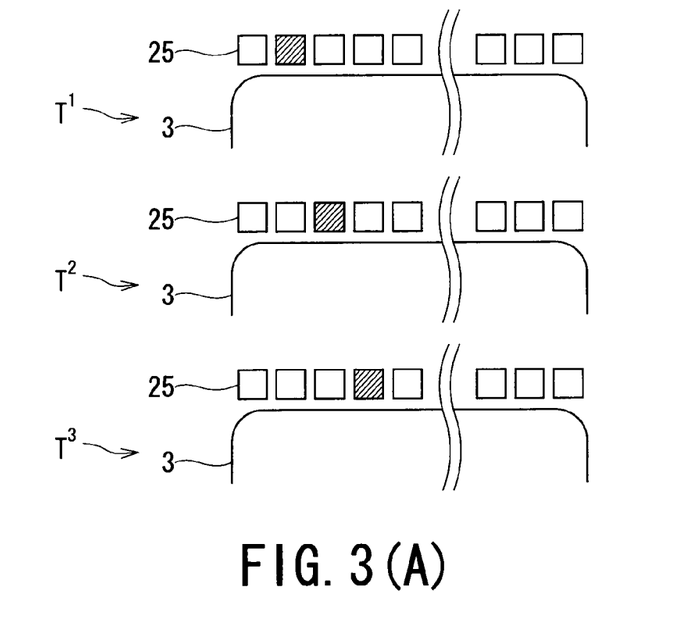
FIG. 3(A) illustrates ultrasonic scans by piezoelectric element array.

As shown in FIG. 3(A), the element driving unit 11 scans the piezoelectric element array 25 at a predetermined cycle to transmit ultrasonic waves to the square billet 3.

Assuming that a sequence number of the piezoelectric element of the array 25 is N and the cycle of the ultrasonic scan is T, a transmission interval $\Delta t$ of the ultrasonic waves between the adjacent piezoelectric element of the array 25 is represented by $\Delta t = T/N$.

As described later, in the element driving unit 11, the cycle T is adjusted so as to prevent multiple reflection of surface echoes from the square billet 3 from affecting an internal image. The adjustment of the cycle T is performed through trial and error in order not to include ghosts of multiple reflections in a synthesized internal image.

It is assumed here that shaded one of the piezoelectric elements of the array 25 in an upper part of FIG. 3(A) is driven.

Figure 3B:
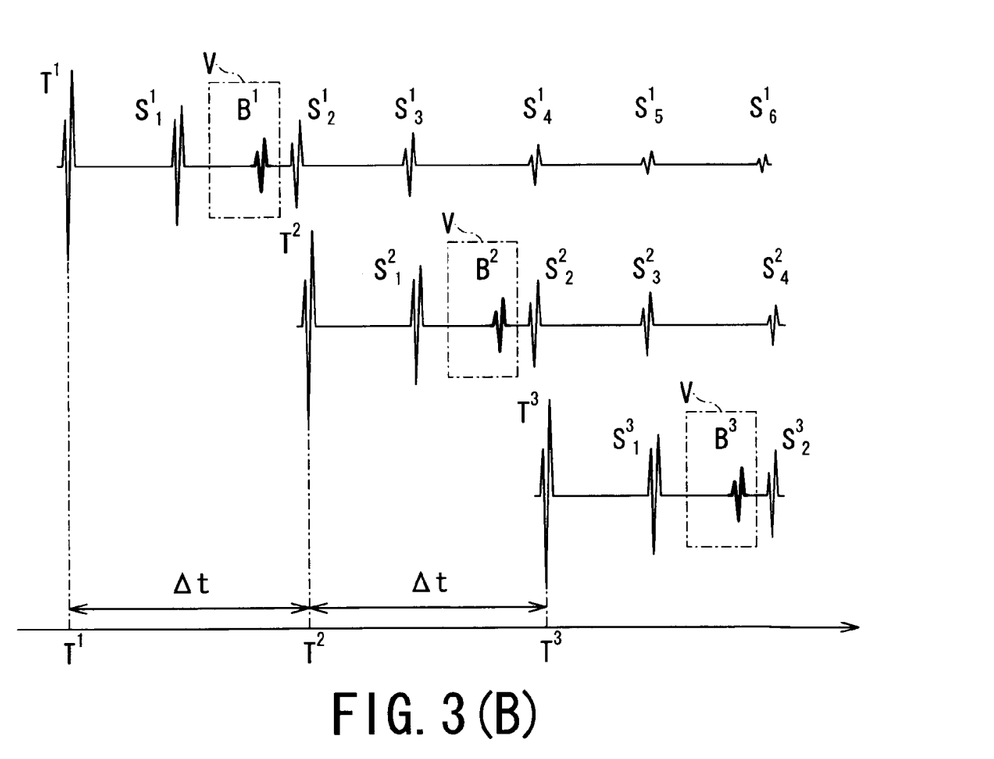
FIG. 3(B) illustrates transmitted ultrasonic waves and received echo signals.

Then, as shown in an upper side of FIG. 3(B), an ultrasonic wave $T^1$ is transmitted, and after a surface echo $S^1{}_1$ is received first, a bottom echo $B^1$ is received. Later, multiple echoes $S^1{}_2$, $S^1{}_3$, $S^1{}_4$, $S^1{}_5$, and $S^1{}_6$ from the surface are sequentially detected with decreasing intensity at a predetermined interval.

After the transmission interval $\Delta t$, shaded one of the piezoelectric element of the array 25 in a middle part of FIG. 3(A) is driven to transmit an ultrasonic wave $T^2$ as shown in a middle of FIG. 3(B). Then, after a surface echo $S^2{}_1$ is received first, a bottom echo $B^2$ is received. Later, multiple echoes $S^2{}_2$, $S^2{}_3$, and $S^2{}_4$ from the surface are sequentially detected with decreasing intensity at the predetermined interval.

Also, after this transmission interval $\Delta t$, this flow is true of a case shown in a lower part of FIG. 3(A) and a lower side of FIG. 3(B).

In these cases, if multiple echoes derived from the previous ultrasonic wave are superimposed on a signal area V, which forms an internal image of the square billet 3, the internal image includes ghosts. Therefore, the cycle T of the ultrasonic scans (or the transmission interval $\Delta t$ of ultrasonic waves from adjacent piezoelectric elements of the array 25) is adjusted so as not to perform a multiple echo derived from the previous ultrasonic wave from being superimposed on a signal area V.

As shown in FIG. 2, the signal detecting unit 12 detects an electrical signal converted from an echo signal U at the piezoelectric element array 25. The weak analog electrical signal detected is amplified at the amplifying unit 13, and then converted into a digital signal at the A/D converting unit 14.

The synthesizing unit 15 synthesizes an internal image of the square billet 3 based on each of the echo signals converted into the digital signals. The synthesizing unit 15, in which an internal parallel processor, processes input digital signals synthetically using the synthetic aperture focusing technique (SAFT) and generate three-dimensional image information interior of the square billet 3 is visualized.

The replacement setting unit 16 determines a threshold value or a maximum peak of an echo signal and sets a certain range including and around the determining point as a range of the bottom echo described later based on FIG. 5(B).

Figure 5A:
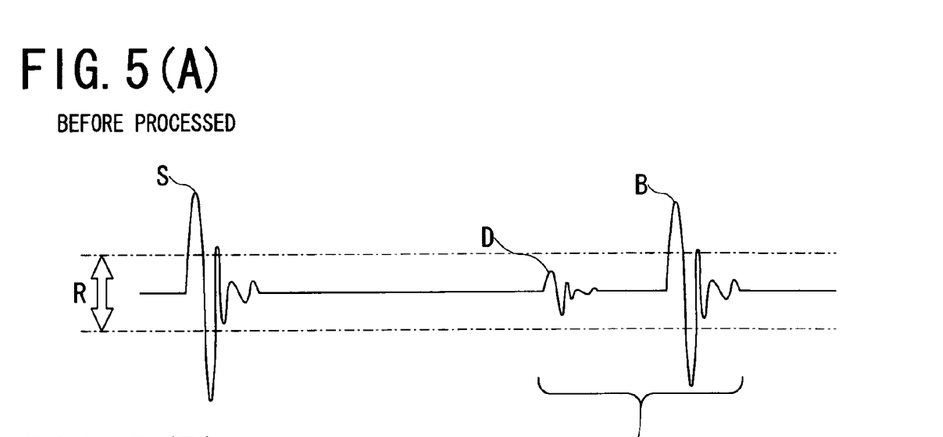
FIG. 5(A) illustrates echo signals that have not yet been processed by a signal replacing unit.
Figure 5B:
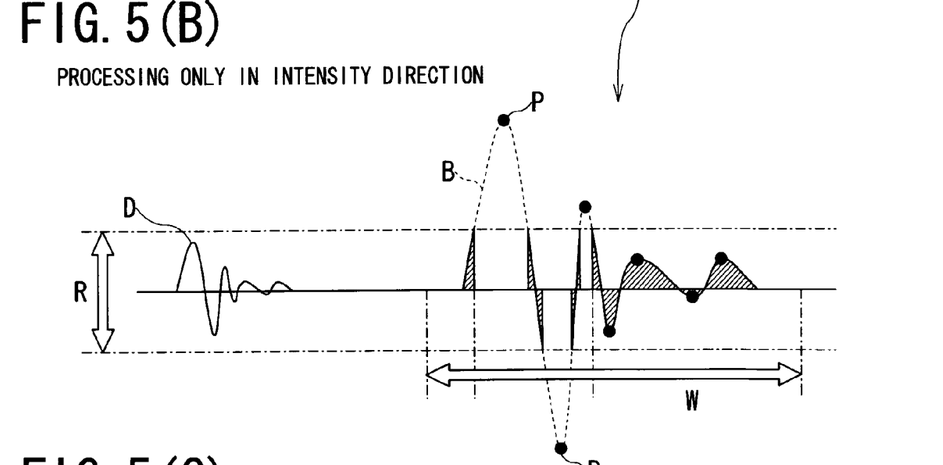
FIG. 5(B) illustrates the processing by the signal replacing unit.
Figure 5C:
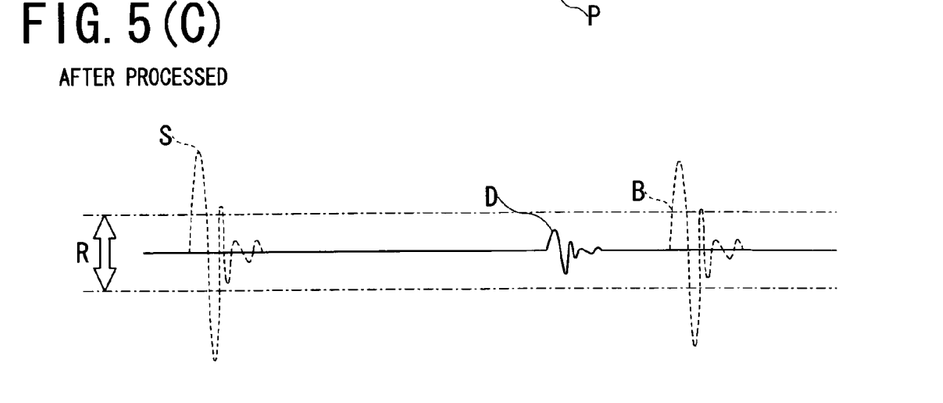
FIG. 5(C) illustrates the echo signals that have been processed by the signal replacing unit.

The signal replacing unit 17 replaces a received echo signal (FIG. 5(A)) with an echo signal (FIG. 5(C)) in which a bottom echo of the square billet 3 has been removed.

Figure 4:
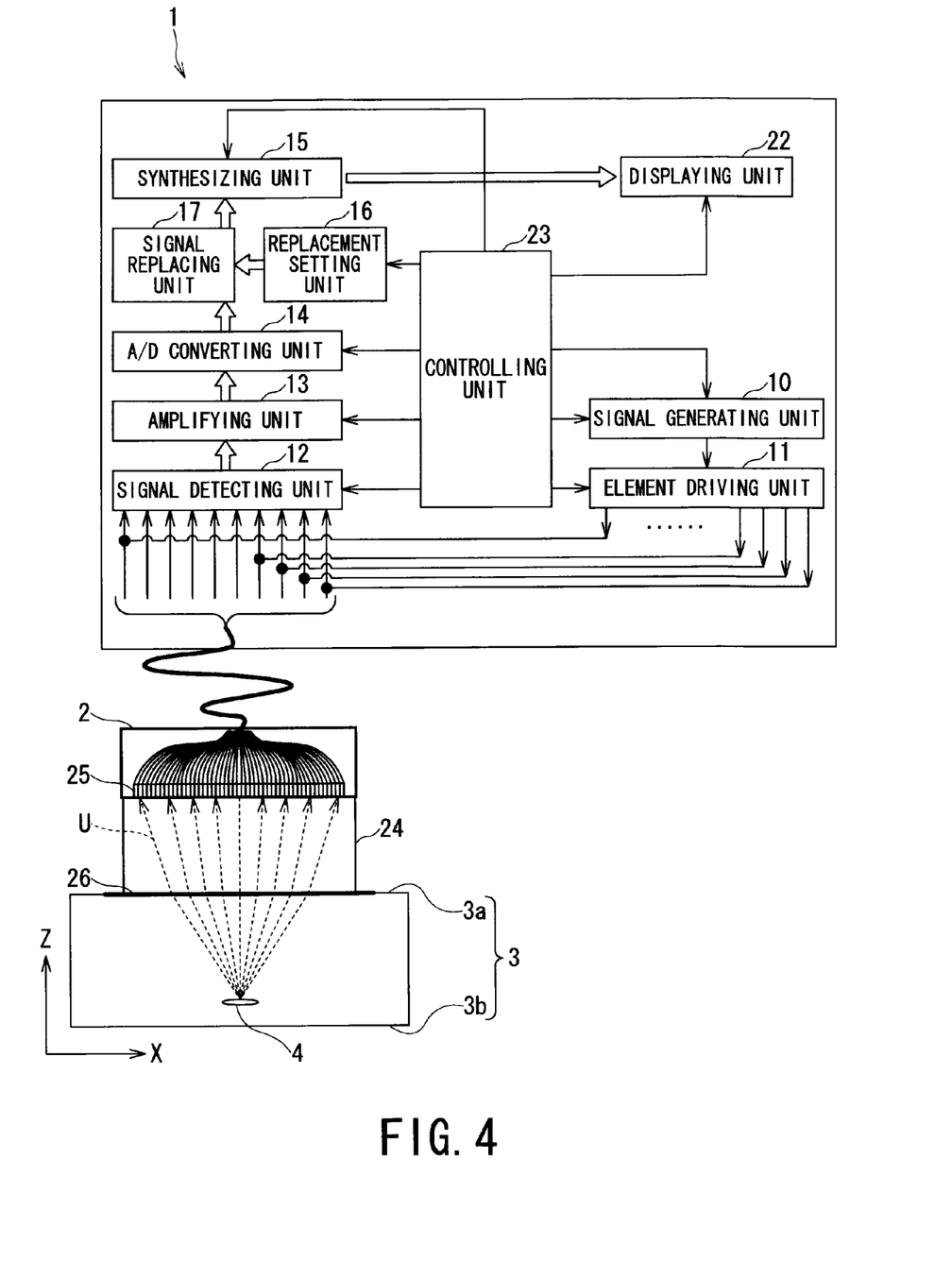
FIG. 4 is a block diagram illustrating a modified example of the ultrasonic flaw detecting apparatus in accordance with the first embodiment.

It should be noted that FIG. 2 shows that the signal replacing unit 17 performs the replacement after an echo signal is input to the synthesizing unit 15, but as shown in a modified example of FIG. 4, the signal replacing unit 17 may perform the replacement before an echo signal is input to the synthesizing unit 15.

The synthesizing unit 15 has a function to, if such signal replacing is performed, modify pixel signals of an internal image synthesized from portions in which bottom echoes are removed, to an average intensity level of neighboring pixel signals.

This avoids a case in which if synthesizing is executed with a signal of a bottom echo simply reset to zero, three-dimensional image information of a corresponding portion is different from a flawless normal portion.

Next, operations of the replacement setting unit 16 and the signal replacing unit 17 will be described with reference to FIG. 5.

As shown in FIG. 5(A), echo signals forming three-dimensional image information that have not been processed by the signal replacing unit 17 include waveforms of a surface echo S, a bottom echo B, and a flaw echo D. As a method set at the replacement setting unit 16, for removing the surface echo S and the bottom echo B, a method that uses a threshold value R and a method that detects a peak top P will be illustrated.

First, the method that uses the threshold value R will be described.

The threshold value R is set in the replacement setting unit 16, and the signal replacing unit 17 replaces intensity of signals exceeding the set threshold value R with zero in three-dimensional image information that the synthesizing unit 15 has generated (or echo signals that exist before the three-dimensional image information is generated).

Then, as shown in shaded parts of FIG. 5(B), there remain signal waveforms under the threshold value R around the signals that have been replaced with zero. Because the remaining waveforms may be accidentally detected as a flaw, signal intensity across an extended range W around the signals that exceed the threshold value R is replaced with zero to remove the surface echo S and the bottom echo B.

Next, the method that detects the peak top P will be described.

In this case, the replacement setting unit 16 has a function to set the peak top P of an echo signal. Typically, since intensity of the surface echo S and the bottom echo B is higher than intensity of the flaw echo D, locations of the surface echo S and the bottom echo B can be identified certainly.

To detect a flaw located at a deeper position with high accuracy, it is more important to certainly identify a location of the bottom echo B than the surface echo S. If a shape of the square billet 3, which is the test object, is determined, because an appearance range of the surface echo S and the bottom echo B can also be roughly determined, the peak top P may be detected within the determined appearance range.

It is necessary to replace signal intensity across an extended range W around a signal having the detected peak top P with zero. This is same as the above-mentioned method that uses the threshold value R.

As described above, by the functions of the signal replacing unit 17 that use the method for using the threshold value R and the method for detecting the peak top P, as shown in FIG. 5(C), after the replacement processing, the surface echo S (dashed line) and the bottom echo B (dashed line) are removed from three-dimensional image information, and only the waveform of the flaw echo D is extracted.

The displaying unit 22 (FIG. 2) captures and displays the three-dimensional image information that the signal replacing unit 17 has performed the replacement processing.

Figure 6A:
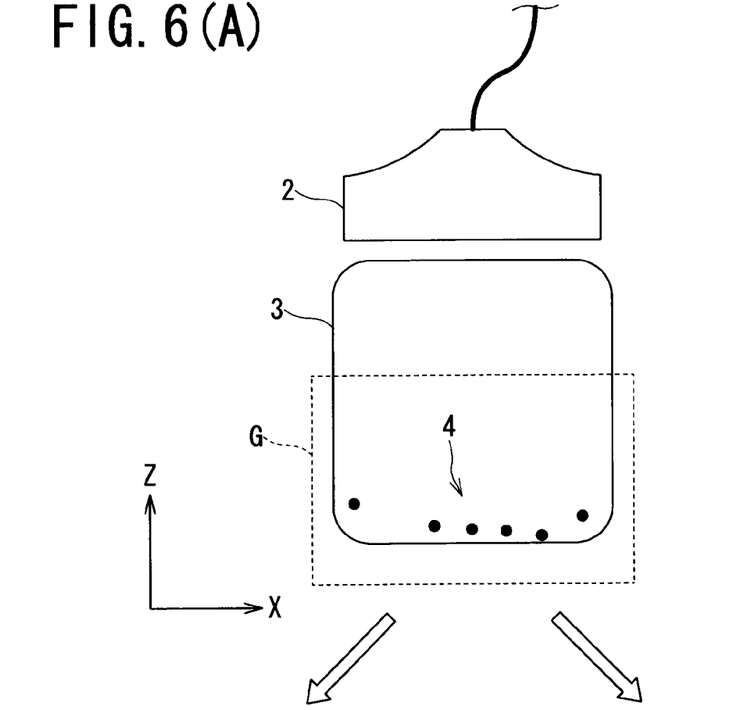
FIG. 6(A) is a conceptual diagram illustrating a distribution of flaws in a test object.
Figure 6B:
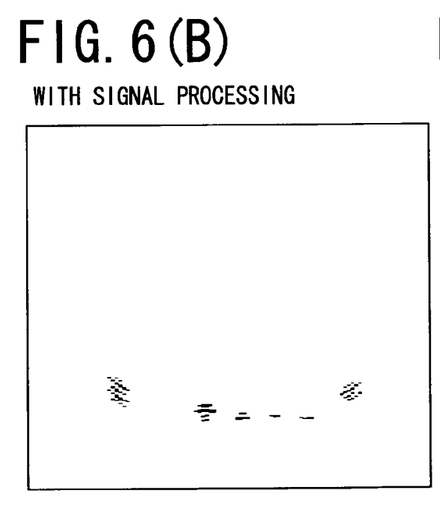
FIG. 6(B) illustrates a visualized flaw distribution in which a bottom echo is removed.
Figure 6C:
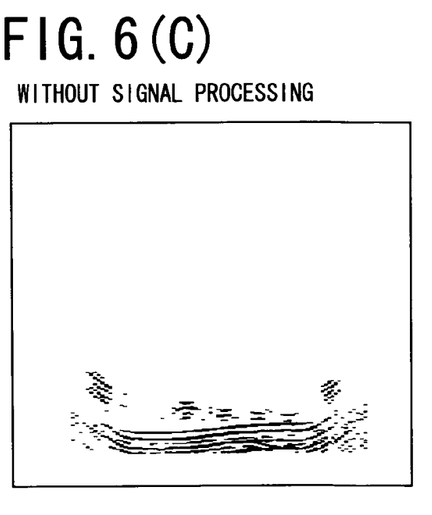
FIG. 6(C) illustrates a visualized flaw distribution in which a bottom echo remains.

FIG. 6(A) conceptually illustrates a distribution of flaws 4 in the square billet 3. FIG. 6(B) shows an image of a visualized flaw distribution in which the signal replacing unit 17 executes the replacement processing to remove a bottom echo. FIG. 6(C) shows a visualized image in which the signal replacing unit 17 does not execute the replacement processing and the bottom echo remains.

Such replacement processing can avoid effect caused by multiple echoes from the bottom to accurately detect the flaws 4 in the square billet 3, which is the test object.

Second Embodiment

Figure 7A:
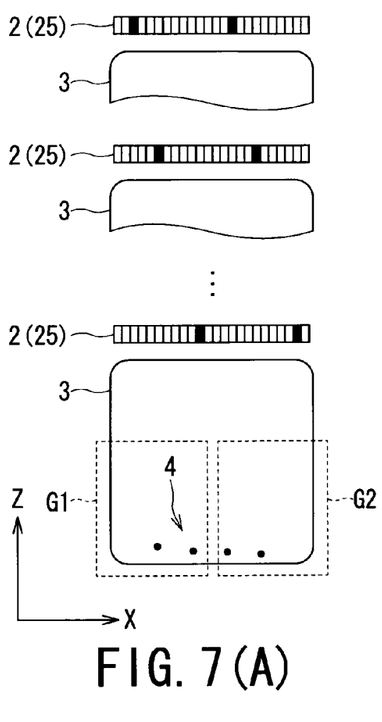
FIG. 7(A) illustrates ultrasonic scans by an ultrasonic flaw detecting apparatus in accordance with a second embodiment.

In the second embodiment, the piezoelectric elements array 25 are divided into at least two areas (in an example of FIG. 7(A), divided into two areas) and the element driving unit 11 performs ultrasonic scans at each area.

The square billet 3 having a flaw distribution conceptually illustrated in FIG. 7(A) is divided into two areas G1 and G2, and then the ultrasonic scans are performed. In this case, because a cycle of the ultrasonic scans is half a cycle of the non-division case (multiplied by a reciprocal number to a division number), a test time of the square billet 3 can be reduced.

Figure 7B:
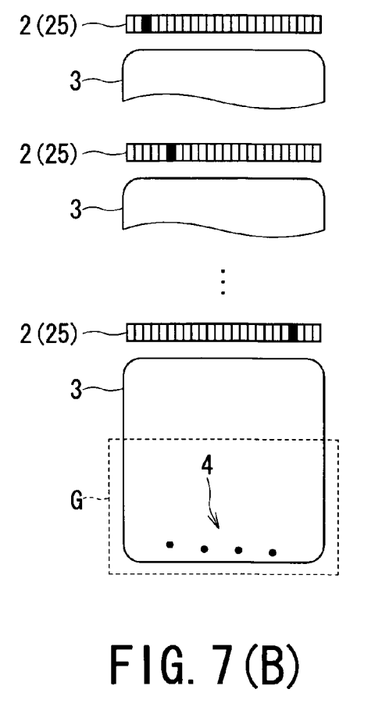
FIG. 7(B) illustrates ultrasonic scans in a comparative example.
Figure 7C:
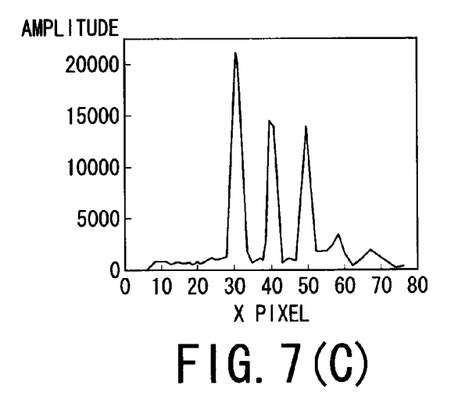
FIG. 7(C) is a graph showing a distribution of pixel intensity of an internal image synthesized in the second embodiment.
Figure 7D:
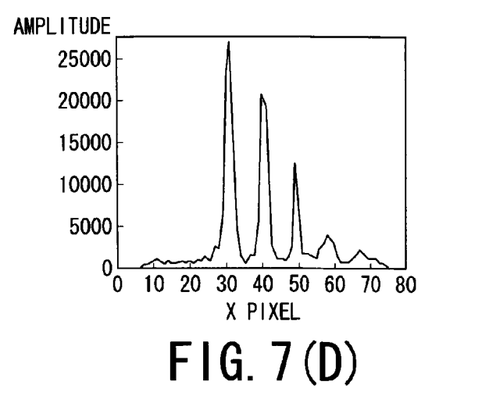
FIG. 7(D) is a graph showing a distribution of pixel intensity of an internal image synthesized in the comparative example.

FIG. 7(C) is a distribution graph of pixel intensity in the case where the synthesizing is performed with such division scans, and signals corresponding to four flaws 4 are significantly detected. The resultant distribution is not much different from a pixel intensity distribution (FIG. 7(D)) of the case in which division scans are not performed on an area G (FIG. 7(B)) as a comparative example.

Third Embodiment

Figure 8A:
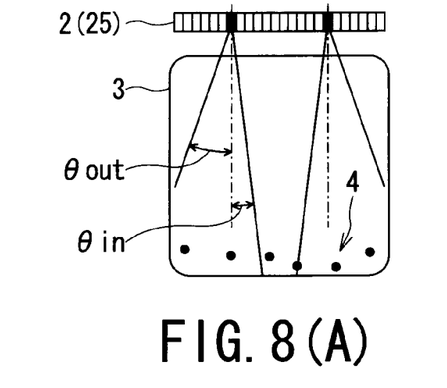
FIG. 8(A) illustrates ultrasonic scans by an ultrasonic flaw detecting apparatus in accordance with a third embodiment.

In the third embodiment, synthesizing unit 15 synthesizes broadly an area closer to a corner relative to an opposite area bordered by a perpendicular line from each of the piezoelectric elements of the array 25.

Figure 8B:
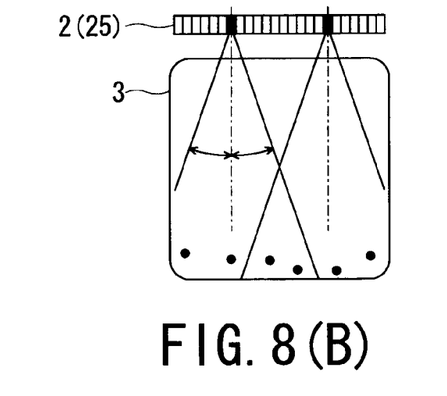
FIG. 8(B) illustrates ultrasonic scans in a comparative example.
Figure 8C:
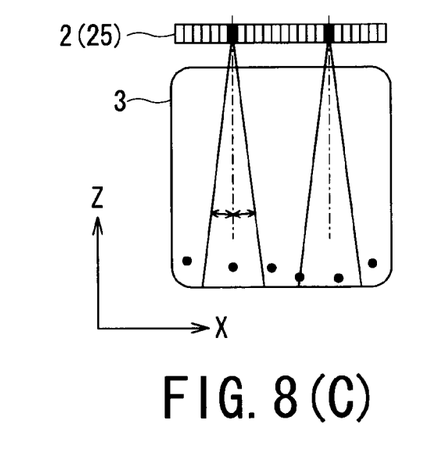
FIG. 8(C) illustrates ultrasonic scans in another comparative example.
Figure 8D:
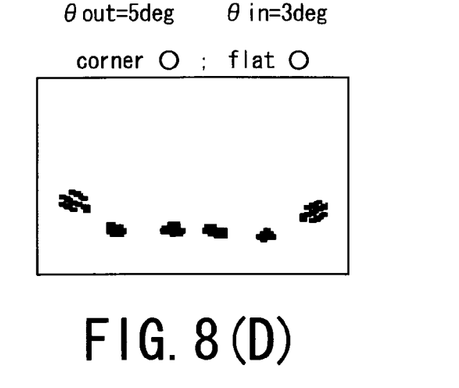
FIG. 8(D) is an internal image synthesized in the third embodiment of FIG. 8(A)

Specifically, as shown in FIG. 8(A), an image of a square billet 3 in which flaws 4 are distributed was synthesized with the area closer to the corner having an angle of 5° and an area closer to a center having an angle of 3°, i.e., with an outward area having a wider angle. As a result, as shown in FIG. 8(D), a resultant image shows that the flaw images at or near the corner and a flat portion are clear.

On the other hand, comparative examples are shown as a case in which area to be synthesized is symmetrical to a perpendicular line from each of the piezoelectric element of the array 25.

Figure 8E:
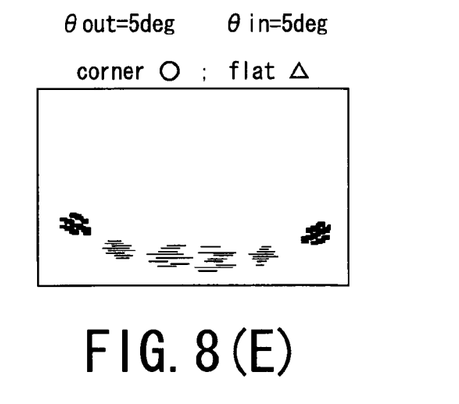
FIG. 8(E) is an internal image synthesized in the comparative example of FIG. 8(B)

If both angle of an area closer to a corner and an area closer to a center are set wide to 5° (FIG. 8(B)), in a resultant image, flaw images at or near the corner were clear, but flaw images at or near a flat portion were obscure (FIG. 8(E)). It is considered that the deterioration of image quality was caused by too increased synthesized images that form the flat portion.

Figure 8F:
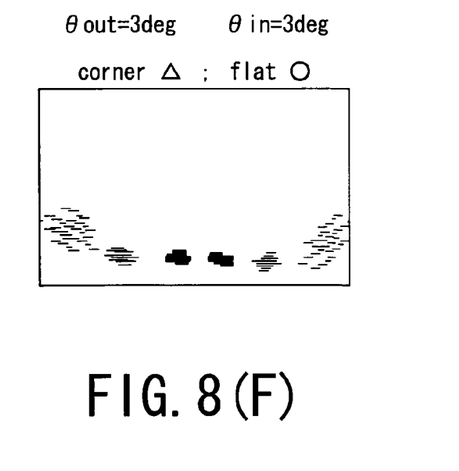
FIG. 8(F) is an internal image synthesized in the comparative example of FIG. 8(C)

If both angle of an area closer to a corner and an area closer to a center were set narrow to 3° (FIG. 8(C)), in a resultant image, flaw images at or near a flat portion were clear, but flaw images at or near the corner were obscure (FIG. 8(F)). It is considered that the deterioration of image quality was caused by too decreased synthesized images that form the corner.

Fourth Embodiment

Figure 9A:
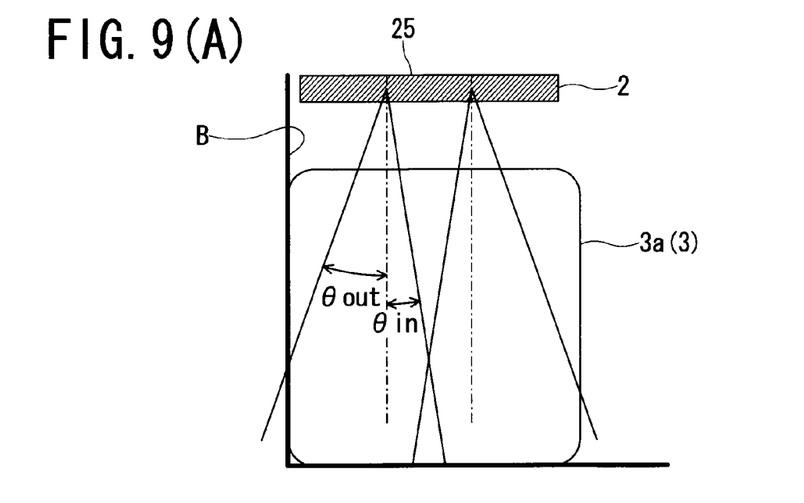
FIG. 9(A) illustrates ultrasonic scans by an ultrasonic flaw detecting apparatus in accordance with a fourth embodiment.
Figure 9B:
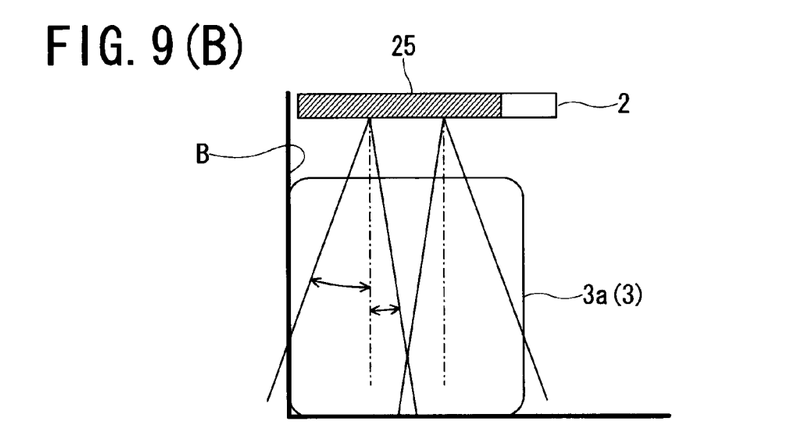
FIG. 9(B) illustrates ultrasonic scans by the ultrasonic flaw detecting apparatus in accordance with the fourth embodiment.
Figure 9C:
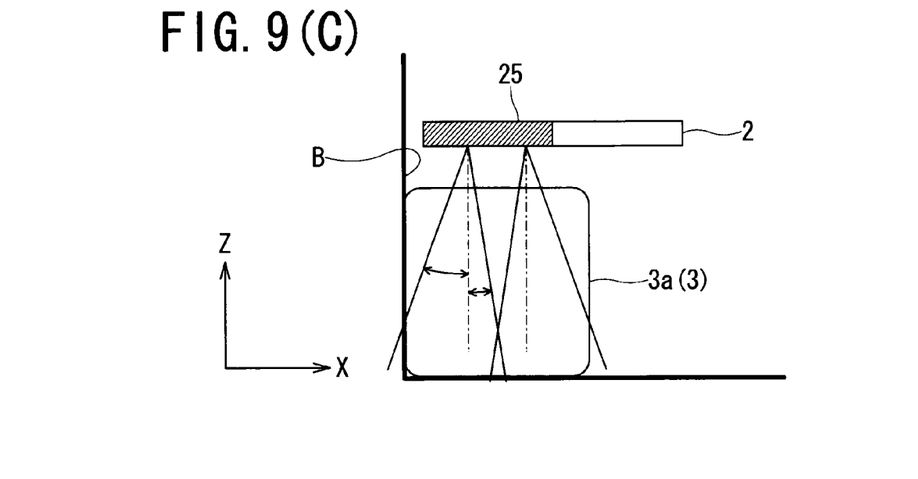
FIG. 9(C) illustrates ultrasonic scans by the ultrasonic flaw detecting apparatus in accordance with the fourth embodiment.

In the fourth embodiment, the element driving unit 11 operates with a range of transmitting and receiving of the piezoelectric element array 25 changed according to the size of the square billet 3.

As shown in FIGS. 9(A), 9(B), and 9(C), this allows for ultrasonic flaw detection of square billets 3a, 3b, and 3c of unequal size without moving the transducer 2.

In addition, in the fourth embodiment, the division scans shown in the second embodiment and the synthesis of an image having a wider angle in an outward area shown in the third embodiment can be performed for square billets 3 of unequal size.

Fifth Embodiment

Figure 10:
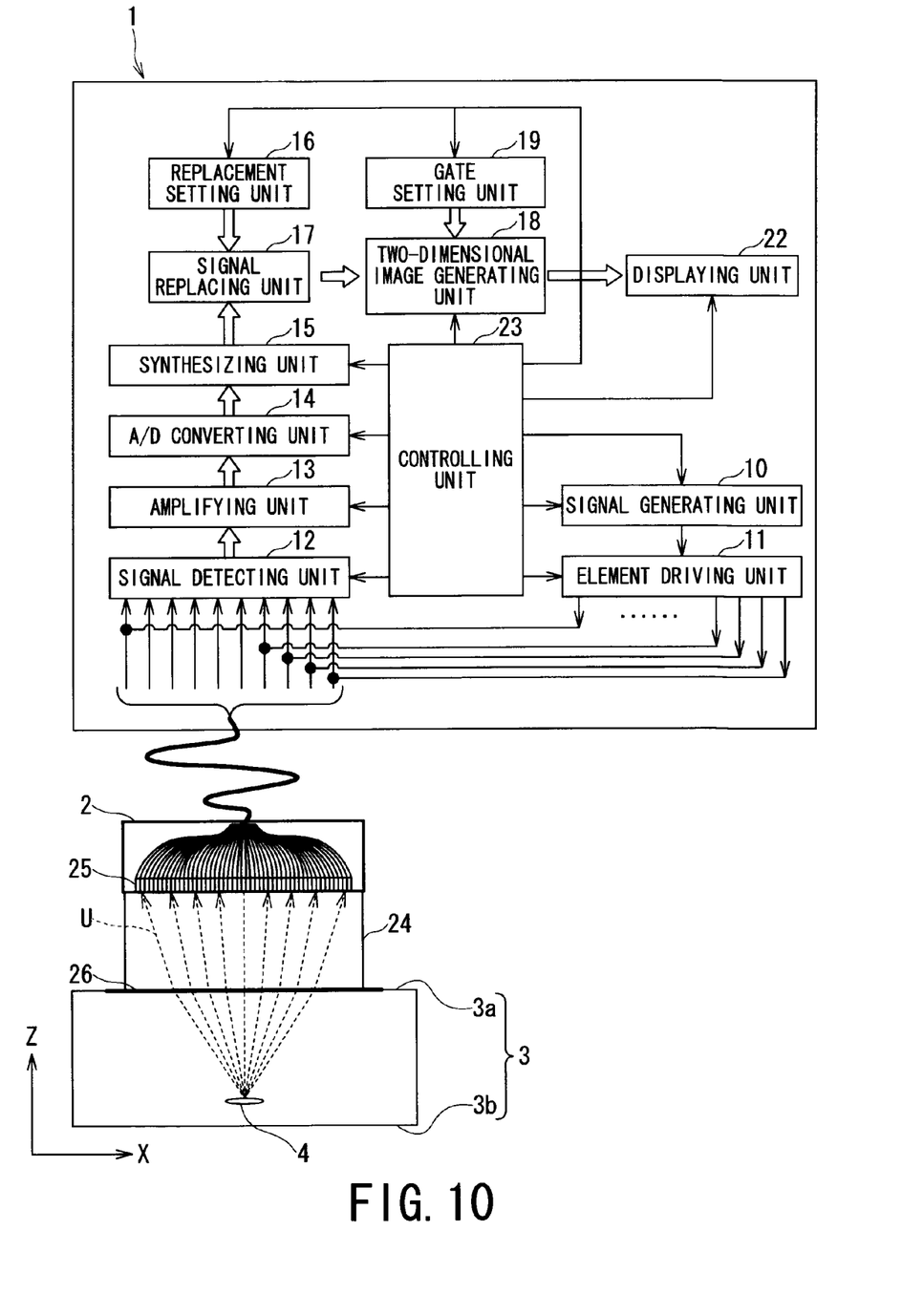
FIG. 10 is a block diagram of an ultrasonic flaw detecting apparatus in accordance with a fifth embodiment.

FIG. 10 is the block diagram of the ultrasonic flaw detecting apparatus in accordance with the fifth embodiment. Note that in FIG. 10, same or corresponding portions as those shown in FIG. 2 are denoted by same reference numerals, and detailed descriptions of these portions will be omitted by citing the above-described descriptions.

The ultrasonic flaw detecting apparatus in accordance with the fifth embodiment further includes a two-dimensional image generating unit 18 and a gate setting unit 19.

The two-dimensional image generating unit 18 generates a perspective image of a test object parallel to a surface 3a or a bottom 3b from three-dimensional image information synthesized by the synthesizing unit 15. That is, in FIG. 10, the displaying unit 22 displays the perspective image showing a distribution of flaws 4 that the square billet 3 is seen along a direction parallel to an XY plane. This allows for easy recognition of locations of the distributed flaws 4 in the square billet 3.

The gate setting unit 19 allows the two-dimensional image generating unit 18 to generate a perspective image for each level in a depth direction. The gate setting unit 19 sets one or more gate ranges in the depth direction (Z direction), and the displaying unit 22 displays an XY plane perspective image of a flaw 4 included in the gate range. This allows for recognition of a flaw distribution for each depth level.

Sixth Embodiment

Figure 11:
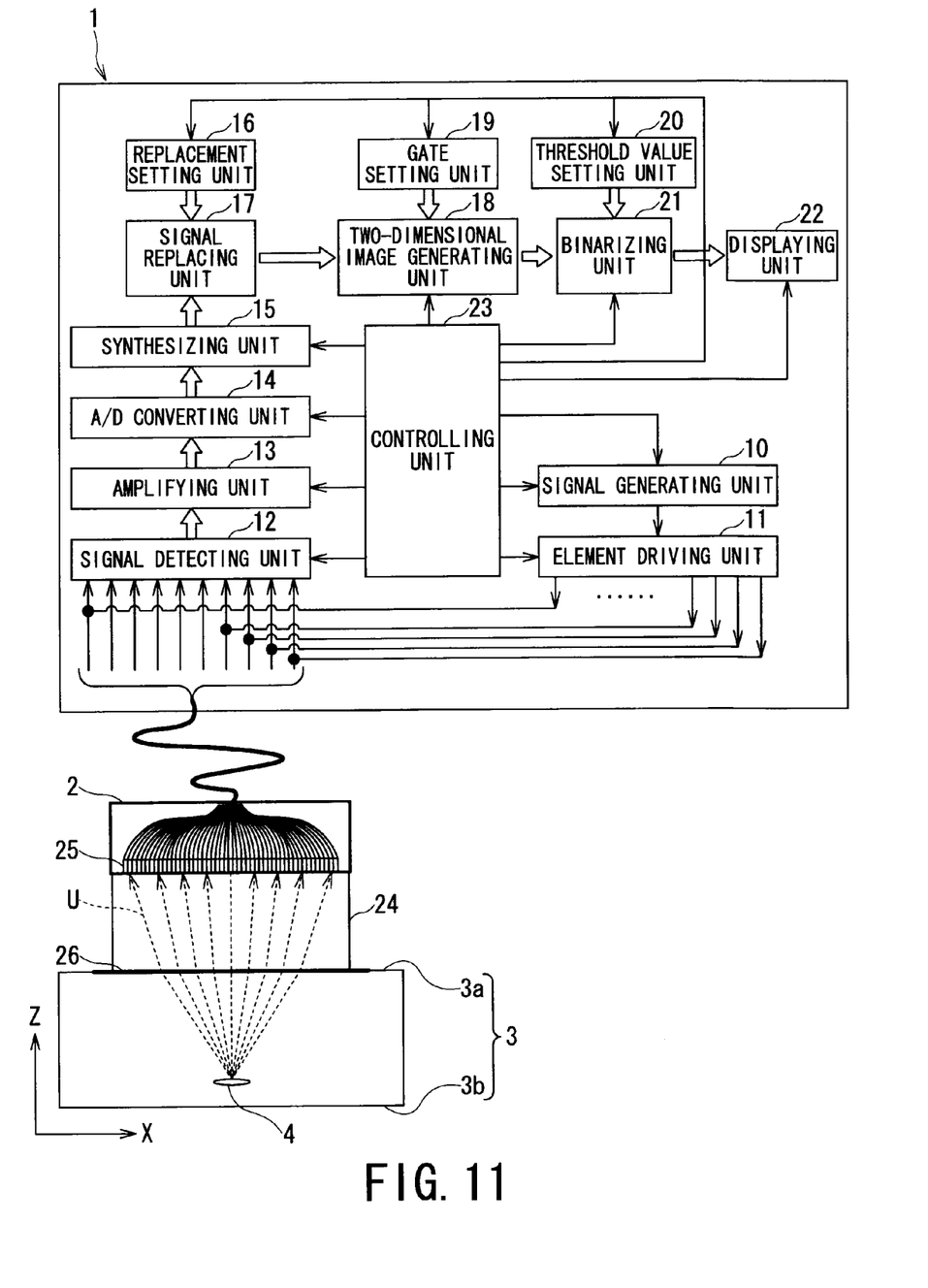
FIG. 11 is a block diagram of an ultrasonic flaw detecting apparatus in accordance with a sixth embodiment.

FIG. 11 is the block diagram of the ultrasonic flaw detecting apparatus in accordance with the sixth embodiment. Note that in FIG. 11, same or corresponding portions as those shown in FIG. 10 are denoted by same reference numerals, and detailed descriptions of these portions will be omitted by citing the above-described descriptions. The ultrasonic flaw detecting apparatus in accordance with the sixth embodiment further includes a threshold value setting unit 20 and a binarizing unit 21.

The binarizing unit 21 represents the internal image as a binary image with binarized brightness levels, and the threshold value setting unit 20 sets a threshold value of the brightness level to obtain the binary image.

The binarizing unit 21 extracts a portion exceeding the threshold value from a two-dimensional image generated by the two-dimensional image generating unit 18 and allows the displaying unit 22 to display the binary image.

This allows for easy recognition and determination of whether the square billet 3 has a flaw 4 or not.

The present invention is not restricted to the embodiments described above, and may be modified as needed within a range of common technical idea. In the embodiments, a square billet is illustrated as a test object, but they may also be applied to a flat plate.

In addition, although apparatuses for online detecting of a flaw in a test object have been illustrated, the present invention can also be applied to an offline apparatus.

While certain embodiments have been described, these embodiments have been presented by way of example only, and are not intended to limit the scope of the inventions. Indeed, the novel apparatus and method described herein may be embodied in a variety of other forms; furthermore, various omissions, substitutions and changes in the form of the apparatus and method described herein may be made without departing from the spirit of the inventions. The accompanying claims and their equivalents are intended to cover such forms or modifications as would fall within the scope and spirit of the inventions.

What is claimed is:

1. An ultrasonic flaw detecting apparatus comprising:
    a transducer in which a piezoelectric element array for transmitting ultrasonic waves to and receiving echo signals from a test object;
    an element driving unit for scanning the piezoelectric element array at a predetermined cycle and causing the ultrasonic waves;
    a synthesizing unit for synthesizing an internal image of the test object based on the echo signals received by the piezoelectric element array;
    a signal replacing unit for replacing the received echo signal with an echo signal in which a bottom echo of the test object is removed; and
    a replacement setting unit for comparing the received echo signals with a determined threshold value or determining a maximum peak of the received echo signals and setting a certain range including, around, and exceeding the threshold value or the maximum peak to a range of the bottom echo,
    wherein the element driving unit adjusts the cycle to prevent multiple reflection of surface echoes from the test object from affecting the internal image.

2. The ultrasonic flaw detecting apparatus according to claim 1, wherein the signal replacing unit performs the replacement before or after the echo signal is input to the synthesizing unit.

3. The ultrasonic flaw detecting apparatus according to claim 1, wherein the synthesizing unit modifies pixel signals of the internal image synthesized from portions in which the bottom echoes are removed, to an average intensity level of neighboring pixel signals.

4. The ultrasonic flaw detecting apparatus according to claim 1, wherein the synthesizing unit synthesizes broadly an area closer to a corner of the test object relative to an opposite area bordered by a perpendicular line from each of the piezoelectric elements of the array.

5. The ultrasonic flaw detecting apparatus according to claim 1, wherein the element driving unit performs the scans with the piezoelectric element array dividing the test object into at least two areas.

6. The ultrasonic flaw detecting apparatus according to claim 1, wherein the element driving unit changes a range of the transmitting and the receiving of the piezoelectric element array according to a size of the test object.

7. The ultrasonic flaw detecting apparatus according to claim 1, further comprising a two-dimensional image generating unit for generating, from the internal image synthesized by the synthesizing unit, a perspective image parallel to the surface or the bottom of the test object.

8. The ultrasonic flaw detecting apparatus according to claim 7, further comprising a gate setting unit for allowing the perspective image to be generated for each level in a depth direction.

9. The ultrasonic flaw detecting apparatus according to claim 1, further comprising a binarizing unit for representing the internal image with binarized brightness levels.

10. An ultrasonic flaw detecting method comprising:
    setting a test object to a transducer in which a piezoelectric element array for transmitting ultrasonic waves and receiving echo signals;
    scanning the piezoelectric element array at a predetermined cycle and causing the ultrasonic waves;
    synthesizing an internal image of the test object based on the echo signals received by the of piezoelectric element array;
    replacing the received echo signal with an echo signal in which a bottom echo of the test object is removed; and
    comparing the received echo signals with a determined threshold value or determining a maximum peak of the received echo signals and setting a certain range including around, and exceeding the threshold value or the maximum peak to a range of bottom echo,
    wherein the scanning the piezoelectric element adjusts the cycle to prevent multiple reflection of surface echoes from the test object from affecting the internal image.

* * * * *